(12) United States Patent
Wang et al.

(10) Patent No.: US 7,915,313 B2
(45) Date of Patent: Mar. 29, 2011

(54) INHIBITORS OF YEAST FILAMENTOUS GROWTH AND METHOD OF THEIR MANUFACTURE

(75) Inventors: Lian-Hui Wang, Singapore (SG); Lian-Hui Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1388 days.

(21) Appl. No.: 11/401,643

(22) Filed: Apr. 10, 2006

(65) Prior Publication Data
US 2006/0260007 A1 Nov. 16, 2006

Related U.S. Application Data

(63) Continuation of application No. PCT/SG2004/000321, filed on Oct. 6, 2004.

(30) Foreign Application Priority Data

Oct. 10, 2003 (SG) .............................. 200305940-9

(51) Int. Cl.
*A61K 31/20* (2006.01)
*C07C 61/08* (2006.01)
*C07C 61/00* (2006.01)

(52) U.S. Cl. .......................... 514/560; 514/558; 562/400
(58) Field of Classification Search .................. 514/558, 514/560; 562/400
See application file for complete search history.

(56) References Cited

U.S. PATENT DOCUMENTS

2002/0086041 A1 7/2002 Maignan et al.

FOREIGN PATENT DOCUMENTS

| EP | 0 568 307 A1 | 11/1993 |
|---|---|---|
| EP | 0 709 092 A1 | 10/1995 |
| EP | 1149880 A1 | 10/2001 |
| JP | 58-213716 | 10/1983 |

OTHER PUBLICATIONS

English Translation (JP58213716) Dec. 12, 1983, Iwamura pp. 1-17.*
Langner et al., 4-Oxatetradecanoic Acid Is Fungicidal for Cryptococcus neoformans and Inhibits Replication of Human Immunodeficiency Virus I, Journal of Biological Chemistry vol. 267 No. 24 (1992) pp. 17159-17169.
Wang et al., A Bacterial Cell-cell Communication Signal with Cross-kingdom Structural Analogues, Molecular Microbiology vol. 51(3) (2004) pp. 903-912.
Barber, et al., A novel regulatory system required for 20 pathogenicity of Xanthomonas campestris is mediated by a small diffusible signal molecule,. Mol Microbiol. (1997) 24(3):555-566.
Brown, Alistair J.P. and Neil A.R. Gow, Regulator networks controlling Candida albicans morphogenesis, Trends Microbiol. (1999) 7(8):333-338.
Brown, et al., Diastereoselective synthesis of tetrahydrofuran-containing fragments by the permanganate oxidation of 1, 5,9-trienes, Chem. Commun. (2000) 1735-1736.
Chiang, John Y.L., Bile acid regulation of gene expression : roles of nuclear hormone receptors, Endocrine Reviews (2002) 23(4):443-463.
Corner, Brian. E. and P.T. Magee, Candida pathogenesis : unraveling the threads of infection., Current Biology, (1997) 7(11):R691-R694.
Forman, et al., Identification of a nuclear receptor that is activated by farnesol metabolites, Cell (1995) 81:687-693.
Kim, et al., Evaluation of morphogenic regulatory activity of farnesoic acid and its derivatives against Candida albicans dimorphism, Bioorgic & Meicianl Chemistry Letters (2002) 12:895-898.
Liu, Haoping, Co-regulation of pathogenesis with dimorphism and phenotypic switching in Candida albicans, a commensal and a pathogen, Int. J. Med. Microbiol. (2002) 292, 299-311.
Madhani, H. D. and G.R. Fink, The control of filamentous differentiation and virulence in fungi, Trends Cell Biol (1998) 8, 348-353.
McGeady, et al., Carvone and perillaldehyde interfere with the serum-induced formation of filamentous structures in Candida albicans at substantially lower concentrations than those causing significant inhibition of growth, J. Nat. Prod (2002) 65:953-955.
Mittendorf et al., Novel antifungal beta-amino acids: synthesis and activity against Candida albicans, Bioorganic & Medicinal Chemistry Letters (2003) 13:433-436.
Navarro-Garcia, et al., Virulence genes in the pathogenic yeast Candida albicans, FEMS Microbial. Rev. (2001) 25:245-268.
Oh et al., Purification and characterization of an autoregulatory substance capable of regulating the morphological transition in Candida albicans, Proc. Natl. Acad. Sci. U.S.A. (2001) 98(8):4664-4668.
Rappe, C., Org. Synth. (1973) 53:123-127.
Rappe, C. and R. Adestrom, Favorsky rearrangements IV. The preparation of some cis-cL, (3-unsaturated acids, Acta Chem Scand. (1965) 19:383-389.
Staib et al., Differential activation of a Candida albicans virulence gene family during infection, Proc. Natl Acad. Sci. U. S. A. (2000) 97(11):6102-6107.
Weinberger, C., A model for farnesoid feedback control in the mevalonate pathway, Trends Endocrinol. Metab. (1996) 7(1):1-6.
Dow et al., Biofilm dispersal in Xanthomonas campestris is controlled by cell-cell signaling and is required for full virulence to plants, Proc. Natl Acad. Sci. USA, (2003) 100(19):10995-11000.
Cason, James and C. Freeman Allen, "Synthesis and Properties of L(+)-2,4-Dimethyl-2-Dodecenoic Acid", Journal of Biological Chemistry, 205:449-457 (1953).
Chhabra et al., "Synthetic Analogues of the Bacterial Signal (Quorum Sensing) Molecule N-(3-Oxododecanoyl)-L-homoserine Lactone and Immune Modulators", J. Med. Chem., 46:97-104 (2003).
Hornby et al., "Quorum Sensing in the Dimorphic Fungus Candida albicans in Mediated by Farnesol", Applied and Environmental Microbiology, 67:2982-29992 (2001).
Shchepin et al., "Quorum Sensing in Candida albicans: Probing Farnesol's Mode of Action with 40 Natural and Synthetic Farnesol Analogs", Chemistry & Biology, 10:743-750 (2003).

* cited by examiner

*Primary Examiner* — Jennifer M Kim
(74) *Attorney, Agent, or Firm* — Michael A. Whittaker; BioTechnology Law Group

(57) ABSTRACT

The invention broadly relates to the use of α,β-unsaturated fatty acids to inhibit the filamentous growth of fungi and yeasts and to a method for producing same. In particular the invention relates to the use of optionally substituted C8 to C15 α,β-unsaturated fatty acids or salts, esters or amides thereof for inhibiting or retarding the yeast-to-mycelium transition of organisms having a dimorphic life cycle.

2 Claims, 3 Drawing Sheets

| Compound | Structure | IC$_{90}$ (μM) |
|---|---|---|
| 1 | 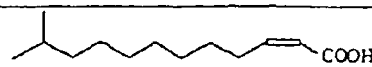 | 15±1 |
| 2 | 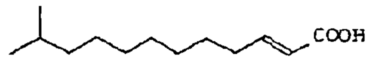 | 15±1 |
| 3 | 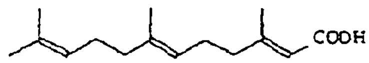 | 3±0.5 |
| 4 | 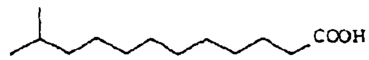 | 100±10 |
| 5 | 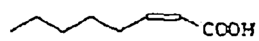 | 60±5 |
| 6 | 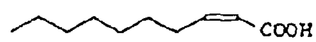 | 45±2 |
| 7 | 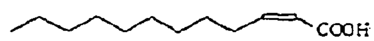 | 40±2 |
| 8 | 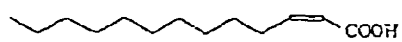 | 80±5 |
| 9 | 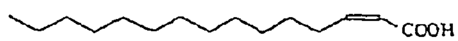 | 100±5 |
| 10 | 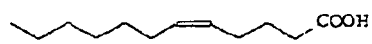 | 100±5 |
| 11 | 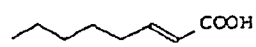 | 65±5 |
| 12 | 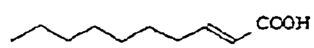 | 43±2 |
| 13 | 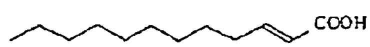 | 40±2 |
| 14 | 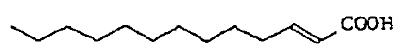 | 80±5 |
| 15 | 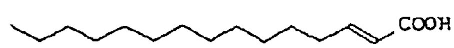 | 100±5 |
| 16 | 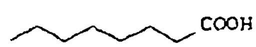 | >500 |
| 17 | 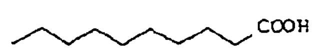 | 150±10 |
| 18 | 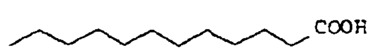 | 150±10 |
| 19 | 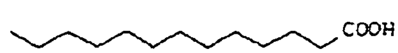 | >500 |
| 20 | 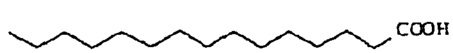 | >500 |

INHIBITORS OF YEAST FILAMENTOUS GROWTH AND METHOD OF THEIR MANUFACTURE

This application is a continuation of PCT/SG04/000321, filed Oct. 6, 2004, which claims priority under 35 U.S.C. §119 of Singapore application no. 200305940-9, filed Oct. 10, 2003.

FIELD OF THE INVENTION

The invention relates to the use of α,β-unsaturated fatty acids to inhibit the filamentous growth of fungi and yeasts and to a method for producing same. In particular the invention relates to the use of optionally substituted $C_8$ to $C_{15}$ fatty acids or salts, esters or amides thereof for inhibiting or retarding the yeast-to-mycelium transition of organisms having a dimorphic life cycle.

BACKGROUND OF THE INVENTION

*Candida albicans*

The dimorphic fungus *Candida albicans* is one of the most significant human fungal pathogens, particularly in immunocompromised patients. This fungus can infect and colonize in a wide range of micro-environments in the body including the blood stream, superficial sites in the mucosa and all of the major internal organs, during systemic infections.[1,2]

A distinguishing feature of *C. albicans* is the yeast-mycelium dimorphism. The yeast-to-mycelium morphogenic transition is one of several essential virulence attributes in human pathogenesis. The yeast-to-mycelium molphogenic transition is triggered by various signals, including serum, high temperature, neutral pH, nutrient poor media, and certain chemicals such as N-acetylglucosamine. It appears that many of the responses to these signals reflect normal interactions between the fungus and its host in vivo.

The yeast-to-mycelium transition has been shown to be one of several virulence attributes that enable *C. albicans* to invade human tissues.[3-5] Patients with serious disease generally have filaments of *C. albicans* penetrating the infected tissue. Various genes involved in hyphal morphogenesis have been identified, including cek1, cla4, cpp1, cst20, and tup1, encoding MAP kinase, PAK, phosphates, MEKK kinase, and transcription factor, respectively. Mutation of these genes blocked *C. albicans* yeast-to-mycelium transition and attenuated its virulence against mouse animal models.[6,7]

Several categories of natural and synthetic chemicals have been evaluated in recent years against *C. albicans* cell growth and dimorphism transition. A novel cyclic β-amino acid that inhibits isoleucyl-tRNA synthetase was shown to inhibit cell growth of *C. albicans*.[8] Carvone and perillaldehyde were found to interfere with the formation of filamentous structures of *C. albicans*.[9]

An autoregulatory substance (ARS) from the eukaryote *C. albicans*, characterized as 3,7,11-trimethyl-2,6,10-dodecatrienoic acid (farnesoic acid), inhibits *C. albicans* germ tube (mycelium) formation and appears to play a key role in the regulation of the morphological transition in *C. albicans*.[10] Its derivatives have been evaluated for their activity in regulation of morphological transitions in *C. albicans* and it was concluded that the trans isomer of farnesoic acid is essential for its potent inhibition of the yeast-to-mycelium transition.[11]

Farnesol, a close derivative of ARS, was shown to prevent mycelial development of *C. albicans* in both growth morphology assay and differentiation assay using three chemically distinct activators for germ tube formation (L-proline, N-acetylglucosamine, and serum).[12]

Farnesol and its metabolite farnesoic acid (ARS) is also found in higher life forms, including humans. They are generated intracellularly and some of the farnesyl derivatives are required for synthesis of cholesterol, steroids, retinoids, and farnesylated proteins.[16,17] Moreover, farnesol metabolites have been implicated as signalling molecules in the regulation of cholesterol degradation through activation of FXR, a nuclear receptor which represses cholesterol metabolism pathway.[16,18] Conceivably, tipping over the subtle balance of these important intermediates and cellular signals may lead to substantial changes in normal physiological processes.

A diffusible signal factor (DSF) from the plant pathogen *Xanthomonas campestris* is a prokaryotic cell-cell communication signal and required for bacterial virulence,[13] but little is known about its structure and scope of function.

Rapid emergence of antibiotic resistance demands development of alternative approaches to prevent and control infectious diseases. As the lethal effect of antibiotics is the common cause to force microbes to mutate and survive, non-antimicrobial means of controlling *C. albicans* and other microorganisms could be useful to avoid or delay the development of antibiotic-resistance. Inhibiting the yeast-to-mycelium transition avoids selection of resistant organisms.

Synthesis of α,β-unsaturated Fatty Acids

Methods for producing short chain (less than 8 carbons) cis-α,β-unsaturated fatty acids using the Favorsky rearrangement of corresponding 1,3-dibromo-2-ones in alkaline solution at room temperature are reported in the art which also reports that best yields are obtained when using potassium bicarbonate.[14,15]

It is an object of the present invention to provide an alternative means for controlling *Candida albicans* infection or to at least provide the public with a useful choice.

SUMMARY OF THE INVENTION

According to a first aspect of the present invention there is provided use of at least one optionally substituted $C_8$ to $C_{15}$ fatty acid or a salt, ester or amide thereof containing only one double bond wherein the double bond is at the α,β-position in the manufacture of a formulation for inhibiting or retarding the yeast-to-mycelium transition of an organism having a yeast-to-mycelium dimorphic life cycle.

A second aspect of the invention provides a method of inhibiting or retarding the yeast-to-mycelium transition of an organism having a yeast-to-mycelium dimomphic life cycle comprising administering to a subject at least one optionally substituted $C_8$ to $C_{15}$ fatty acid or a salt, ester or amide thereof containing only one double bond wherein the double bond is at the α,β-position.

A third aspect of the invention provides a formulation for inhibiting or retarding the yeast-to-mycelium transition of an organism having a yeast-to-mycelium dimorphic life cycle comprising at least one optionally substituted $C_8$ to $C_{15}$ fatty acid or a salt, ester or amide thereof containing only one double bond wherein the double bond is at the α,β-position.

A fourth aspect of the present invention provides use of at least one optionally substituted $C_8$ to $C_{15}$ fatty acid or a salt, ester or amide thereof containing only one double bond wherein the double bond is at the α,β-position in the manufacture of a formulation for treating or preventing an injection by an organism having a yeast-to-mycelium dimorphic life cycle.

A fifth aspect of the invention provides a method treating or preventing an infection by an organism having a yeast-tomycelium dimorphic life cycle comprising administering to a subject at least one optionally substituted $C_8$ to $C_{15}$ fatty acid or a salt, ester or amide thereof containing only one double bond wherein the double bond is at the α,β-position.

A sixth aspect of the invention provides a formulation treating or preventing an infection by an organism having a yeast-to-mycelium dimorphic life cycle comprising at least one optionally substituted $C_8$ to $C_{15}$ fatty acid or a salt, ester or amide thereof containing only one double bond wherein the double bond is at the α,β-position.

The following statements relate to the above aspects of the invention.

In one embodiment, the organism having a yeast-to-mycelium dimorphic life cycle is selected from the group comprising Aspergillus fumigatus, Aureobasidium pullulans, Benjaminiella poitrasii, Blastomyces dermatitidis, Ceratocystis ulmi, Debaryomyces hansenii, Histoplasma capsulatum, Paracoccidioides brasiliensis, Phaeococcomyces exophiale, Sporothrix schenckii, Ustilago maydis, Yarrowia lipolytica and organisms of the Candida genus. A preferred organism of the Candida genus is Candida albicans.

In one embodiment, preferably the fatty acid is a $C_8$ to $C_{13}$ fatty acid. Preferably the fatty acid is a $C_{12}$ fatty acid.

In another embodiment, preferably the fatty acid has at least one substituent. In one embodiment the substituent is a branched alkyl group. Preferably the substituent is an alkyl group, preferably a group selected from the group comprising methyl, ethyl, propyl, butyl, and pentyl, and isomeric forms thereof. It will be apparent to a skilled worker that the fatty acid may have other substituents.

In another embodiment, preferably the fatty acid is selected from the group consisting of:

$(CH_3)_2CH(CH_2)_7CH=CHCOOH$;
$CH_3(CH_2)_4CH=CHCOOH$;
$CH_3(CH_2)_6CH=CHCOOH$;
$CH_3(CH_2)_8CH=CHCOOH$;
$CH_3(CH_2)_9CH=CHCOOH$; and
$CH_3(CH_2)_{11}CH=CHCOOH$.

In another embodiment, preferably the fatty acid is a trans fatty acid.

In another embodiment, preferably the fatty acid is a cis fatty acid.

In another embodiment, preferably the formulation comprises a food, drink, food additive, drink additive, dietary supplement, nutraceutical or pharmaceutical composition. Preferably the pharmaceutical composition comprises a fatty acid of the invention and a pharmaceutically acceptable carrier.

A seventh aspect of the present invention provides a process for producing a cis α,β-unsaturated fatty acid of the formula R—CH=CH—COOH comprising reacting a compound of Formula I:

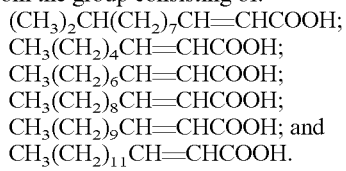

(I)

with:
(1) NaOH; followed by
(2) an acid,
wherein R is an optionally substituted alkyl group and X and Y are independently selected from the group comprising Cl and Br.

In one embodiment, preferably R is optionally substituted $CH_3(CH_2)_{3-10}CH_2$— or $(CH_3)_2CH(CH_2)_{2-9}CH_2$—.

In one embodiment, preferably R is has at least one substituent. In a preferred embodiment the substituent is a branched alkyl group. Preferably the substituent is an alkyl group, preferably a group selected from the group comprising methyl, ethyl, propyl, butyl, and pentyl, and isomeric forms thereof. It will be apparent to a skilled worker that R may have other substituents.

In one embodiment, preferably a compound of formula (I) is reacted with about 0.5, 1, 2, 3, 4, 5 or 6 equivalent NaOH.

In one embodiment, preferably a compound of formula (I) is reacted with NaOH for about 0.5, 1, 2, 3, 4, 5, 6, 7, 8, or 9 hours or longer.

In one embodiment, preferably a compound of formula (I) is reacted with NaOH for about 4 to about 8 hours.

In one embodiment, preferably the acid comprises about 0.5, 1, 1.5 or 2 N HCl.

In one embodiment, preferably a compound of formula (I) is reacted with 4 equivalent NaOH and $H_2O$ for about 6 to about 8 hours followed by neutralization with 1N HCl.

In one embodiment, preferably the process is carried out at about 20 to 30 degrees C.

An eighth aspect of the invention provides a cis α,β-unsaturated fatty acid produced by a process of the invention.

A ninth aspect of the invention provides cis-11-methyl-2-dodecenoic acid.

A tenth aspect of the invention provides trans-11-methyl-2-dodecenoic acid.

An eleventh aspect of the invention provides a pharmaceutical composition comprising cis and/or trans 11-methyl-2-dodecenoic acid and a pharmaceutically acceptable carrier.

A twelfth aspect of the invention provides a pharmaceutical composition comprising a cis and/or trans fatty acid selected from the group comprising $CH_3(CH_2)_4CH=CHCOOH$; $CH_3(CH_2)_6CH=CHCOOH$; $CH_3(CH_2)_8CH=CHCOOH$; $CH_3(CH_2)_9CH=CHCOOH$; and $CH_3(CH_2)_{11}CH=CHCOOH$ and a pharmaceutically acceptable carrier.

This invention may also be said broadly to consist in the part, elements and features referred to or indicated in the specification of the application, individually or collectively, and any or combinations of any two or more said parts, elements or features, and where specifically integers are mentioned herein which have known equivalents in the art to which this invention relates, such known equivalents are deemed to be incorporated herein as if individually set forth.

DETAILED DESCRIPTION OF THE INVENTION

The applicants have found that α,β-unsaturated fatty acids that are structurally dissimilar to ARS have efficacy in inhibiting or retarding the yeast-to-mycelium transition of organisms having a yeast-to-mycelium dimorphic life cycle and that cis isomers also have efficacy contrary to previous reports. Exemplary organisms having a yeast-to-mycelium dimorphic life cycle include organisms of the *Candida* genus such as *Candida albicans*. The invention is also useful in respect of other organisms having a yeast-to-mycelium dimorphic life cycle including but not limited to *Aspergillus fumigatus, Aureobasidium pullulans, Benjaminiella poitrasii, Blastomyces dermatitidis, Ceratocystis ulmi, Debaryomyces hansenii, Histoplasma capsulatum, Paracoccidioides brasiliensis, Phaeococcomyces exophiale, Sporothrix schenckii, Ustilago maydis,* and *Yarrowia lipolytica*. The fatty acids of the invention are thus useful to treat or prevent infection by these organisms.

Fatty acids useful herein include optionally substituted $C_8$ to $C_{15}$ α,β-unsaturated fatty acids or salts, esters or amides thereof containing one double bond wherein the double bond is at the α,β-position. In one embodiment, preferably the fatty acid is a $C_8$ to $C_{13}$ fatty acid. Preferably the fatty acid is a $C_{12}$ fatty acid. Fatty acids useful herein may be substituted or unsubstituted, and cis or trans fatty acids. Fatty acids useful herein include $(CH_3)_2CH(CH_2)_7CH=CHCOOH$; $CH_3(CH_2)_4CH=CHCOOH$; $CH_3(CH_2)_6CH=CHCOOH$; $CH_3(CH_2)_8CH=CHCOOH$; $CH_3(CH_2)_9CH=CHCOOH$; and $CH_3(CH_2)_{11}CH=CHCOOH$. It will be apparent to a skilled worker that the fatty acid may comprise alkyl or other substituents.

The applicants have also elucidated the structure of DSF to be cis-11-methyl-2-dodecenoic acid.

The applicants have also elucidated a novel reaction scheme for high yield production of cis-α,β-unsaturated fatty acids.

The previously reported methods for synthesis of α,β-unsaturated fatty acids can be used for preparation of short-chain cis-α,β-unsaturated fatty acids (less than 8 carbons).[5]

However, it was found that these methods were not suitable for synthesising long-chain cis-α,β-unsaturated fatty acids. For example, under the reported optimal reaction conditions, the yield of cis-2-dodecenoic acid (FIG. 2, compound 7) was found to be less than 5%, even after a prolonged reaction time of up to 96 h (FIG. 1a-first peak cis-2-dodecenoic acid; second peak 1,3-dibromo-2-dodecanone).

Figure 1:
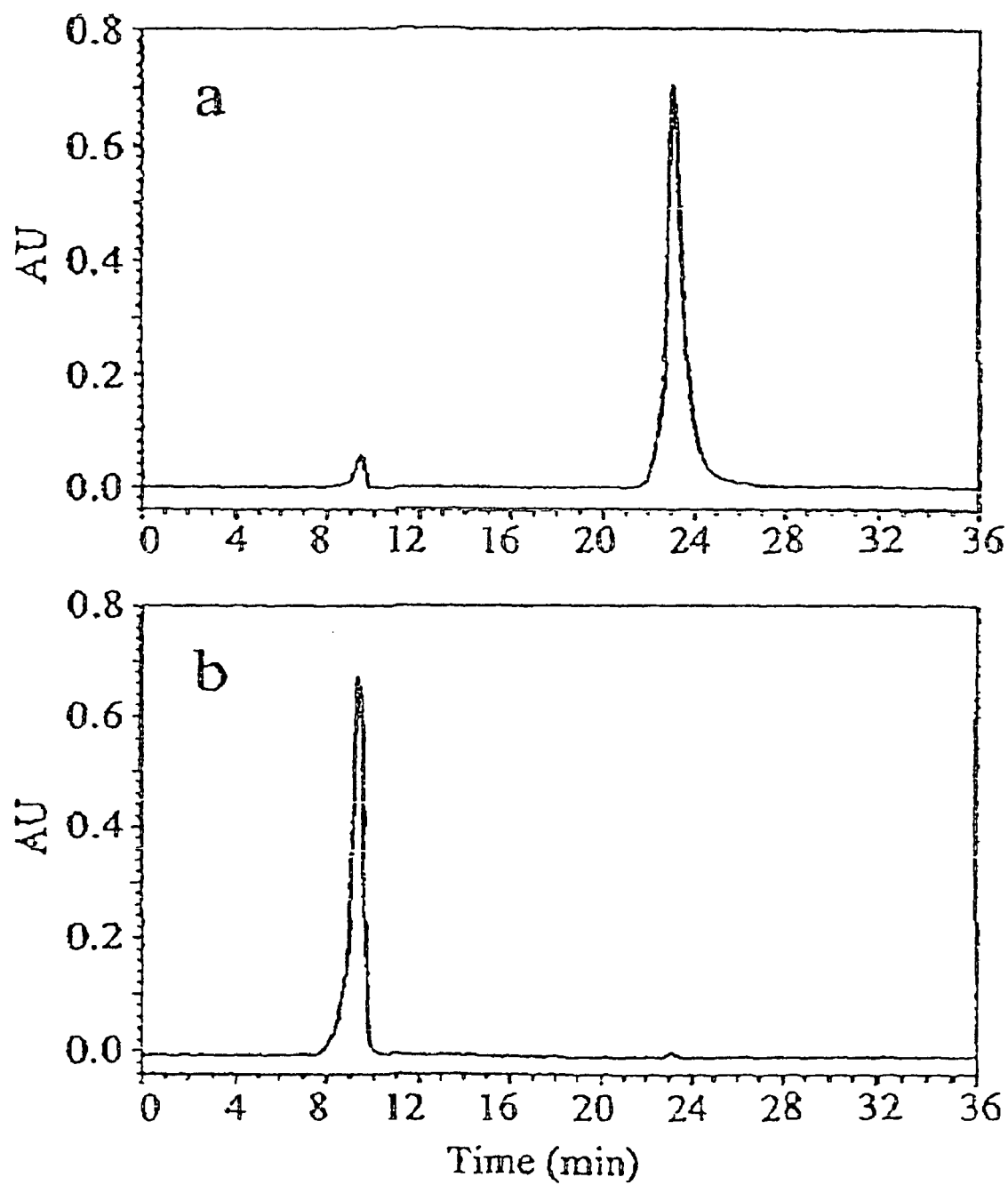
FIG. 1a shows HPLC analysis of the efficiency of synthesising cis-2-dodecenoic acid using a previously reported method.
FIG. 1b shows HPLC analysis of the efficiency of synthesising cis-2-dodecenoic acid using a method of the invention.

It was found that replacing potassium bicarbonate with sodium hydroxide increased the yield of cis-2-dodecenoic acid up to 98% (Scheme 1 and FIG. 1b-first peak cis-2-dodecenoic acid; second peak 1,3-dibromo-2-dodecanone).

Scheme 1

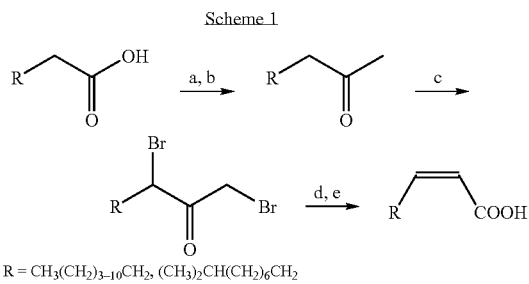

In Scheme 1, (a) LiMe, $CH_3OCH_3$; (b) $H_2O$; (c) $Br_2$, HBr, $H_2O$; (d) NaOH, $H_2O$; (e) HCl.

In preferred embodiment of Scheme 1, (a) LiMe, $CH_3OCH_3$, 4 h; (b) $H_2O$, ~90% yield; (c) $Br_2$, HBr, $H_2O$, 2 h: ~50% yield; (d) NaOH, $H_2O$, 6-8 h; (e) 1N HCl, >85% yield.

Accordingly, in one aspect, the invention provides a process for producing a cis α,β-unsaturated fatty acid of the formula R—CH=CH—COOH comprising reacting a compound of Formula I:

with:
(1) NaOH; followed by
(2) an acid,
wherein R is an optionally substituted alkyl group and X and Y are independently selected from the group comprising Cl and Br.

In one embodiment, preferably R is optionally substituted $CH_3(CH_2)_{3-10}CH_2$— or $(CH_3)_2CH(CH_2)_{2-9}CH_2$—.

In one embodiment, preferably R is substituted. In a preferred embodiment the substitution is a branched alkyl group. Preferably the substituted is an alkyl group, preferably a group selected from the group comprising methyl, ethyl, propyl, butyl, and pentyl, and isomeric forms thereof. It will be apparent to a skilled worker that R may have other substituents.

In one embodiment, preferably a compound of formula (I) is reacted with about 0.5, 1, 2, 3, 4, 5 or 6 equivalent NaOH.

In one embodiment, preferably a compound of formula (I) is reacted with NaOH for about 0.5, 1, 2, 3, 4, 5, 6, 7, 8, or 9 hours or longer.

In one embodiment, preferably a compound of formula (I) is reacted with NaOH for about 4 to about 8 hours.

In one embodiment, preferably the acid comprises about 0.5, 1, 1.5 or 2 equivalent HCl.

In one embodiment, preferably a compound of formula (I) is reacted with 4 equivalent NaOH and $H_2O$ for about 6 to about 8 hours followed by neutralization with 1N HCl.

In one embodiment, preferably the process is carried out at about 20 to 30 degrees C.

To conduct the HPLC analyses depicted in FIGS. 1a and 1b, the reaction products were extracted with hexane, dried, then analyzed using HPLC on a $C_{18}$ reverse-phase column (4.6×250 mm) and eluted with methanol-water (80:20, vol/vol) at a flow rate of 1 ml/min. The retention time was 9.5 min for cis-2-dodecenoic acid, and 23.2 min for 1,3-dibromo-2-dodecanone, respectively.

Figure 2:
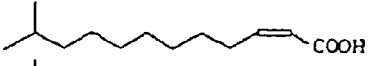
FIG. 2 shows the in vitro inhibitory activity of selected fatty acids against the yeast-to-mycelium transition of Candida albicans.
Figure 2:
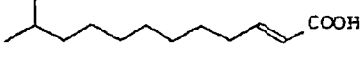
Figure 2:
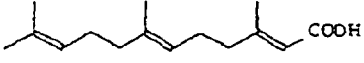
Figure 2:
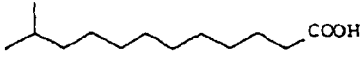
Figure 2:
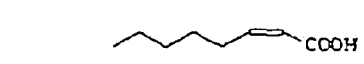
Figure 2:
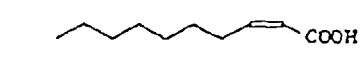
Figure 2:
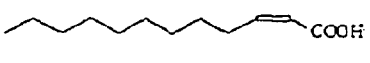
Figure 2:
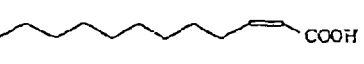
Figure 2:
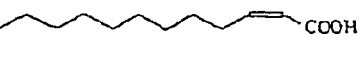
Figure 2:
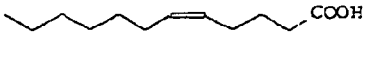
Figure 2:
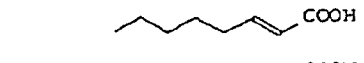
Figure 2:
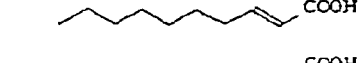
Figure 2:
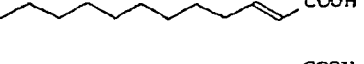
Figure 2:
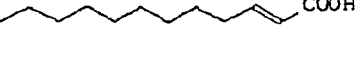
Figure 2:
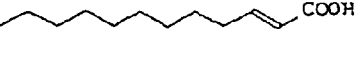
Figure 2:
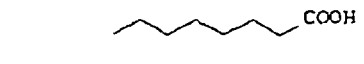
Figure 2:
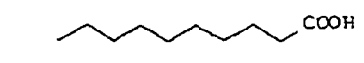
Figure 2:
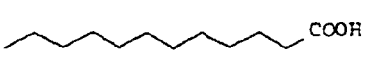
Figure 2:
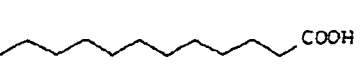
Figure 2:
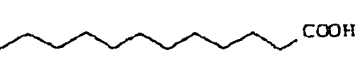

The other long-chain cis-α,β-unsaturated fatty acids of FIG. 2 were also synthesized in high yields using the modified method of Scheme 1 (Table 1).

TABLE 1

Yields of cis-α,β-unsaturated fatty acids produced according to Scheme 1

| | Compound* | | | | | |
|---|---|---|---|---|---|---|
| | 1 | 5 | 6 | 7 | 8 | 9 |
| Yield (%) | 88.3 | 93.9 | 96.5 | 98.1 | 97.2 | 95.5 |

*Compounds are numbered according to FIG. 2. The yield was calculated as a percentage of product/substrate based on HPLC analysis.

The purified reaction products were examined by NMR. In all cases, the chemical shifts and the coupling constants of the protons on the double bond (~11.5 Hz) indicate the products were cis-acids (data not shown).

FIG. 2 shows the in vitro inhibitory activity of selected fatty acids against the yeast-to-mycelium transition of *Candida albicans*, including the cis and trans isomers of DSF (compounds 1 and 2), ARS (compound 3), and compounds produced according to a process of the invention (cis compounds 5 to 9).

Contrary to the previous reports that the trans configuration of the α,β-double bond of ARS is essential for the inhibitory effect against *C. albicans* filamentous growth,[11] DSF and compound 2 (the trans-isomer of DSF) showed an identical inhibitory activity. Moreover, the other cis- and trans-isomer pairs of α,β-unsaturated fatty acids (compounds 5 and 11, 6 and 12, 7 and 13, 8 and 14, 9 and 15) also each showed very similar or identical inhibitory activity (FIG. 2).

As yeast-to-mycelium transition appears to be necessary for the pathogenicity of *C. albicans*, the compounds disclosed herein have utility for the control of the fungal disease. Rapid emergence of antibiotic resistance demands development of alternative approaches to prevent and control infectious diseases. As the lethal effect of antibiotics is the common cause to force microbes to mutate and survive, non-antimicrobial means of controlling *C. albicans* and other microorganisms could be useful to avoid or delay the development of antibiotic-resistance. Inhibiting the yeast-to-mycelium transition provides such a possibility.

The fatty acids useful herein may be incorporated into a food, drink, food additive, drink additive, dietary supplement, neutraceutical or pharmaceutical.

The pharmaceutical compositions provided by the invention comprise a fatty acid of the invention and a pharmaceutically acceptable carrier. The pharmaceutical compositions of the invention can be administered in any suitable manner and thus may be formulated for administration orally, topically, subcutaneously, intramuscularly, intravenously, or parenterally, for example.

The invention consists in the foregoing and also envisages constructions of which the following gives examples only.

Example 1

Scheme 1 and Scheme 2 set out below were employed to synthesize α,β-unsaturated fatty acids listed in FIG. 2. As shown in Scheme 1, cis-α,β-unsaturated fatty acids were synthesized using the Favorsky rearrangement of corresponding 1,3-dibromo-2-ones in alkaline solution at room temperature by modifying a previously reported method.[15,16] Commercially available fatty acids (Sigma-Aldrich, USA) were converted to corresponding methyl ketones in the presence of LiMe. Methyl ketones were reacted with bromide reagents to produce 1,3-dibromo-2-ones which were then rearranged to produce cis-α,β-unsaturated fatty acids in the presence of 4 equivalent NaOH.

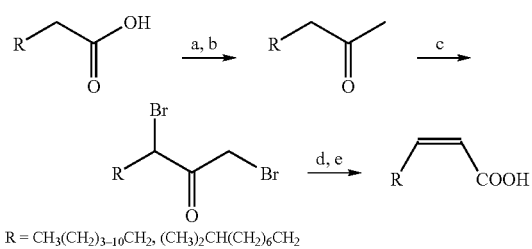

Scheme 1

In Scheme 1, (a) LiMe, CH$_3$OCH$_3$, 4 h; (b) H$_2$O, ~90% yield; (c) Br$_2$, HBr, H$_2$O, 2 h, ~50% yield; (d) NaOH, H$_2$O, 6-8 h; (e) 1N HCl, >85% yield.

Trans-α,β-unsaturated fatty acids were synthesized through elimination of 2-bromo fatty acids prepared by brominating saturated fatty acids, using potassium tert-butoxide as a base in tert-butanol (Scheme 2). The methyl ester of ARS (3,7,11-trimethyl-2,6,10-dodecatrienoic acid) was synthesized as previously reported[16] and then hydrolyzed to produce ARS.

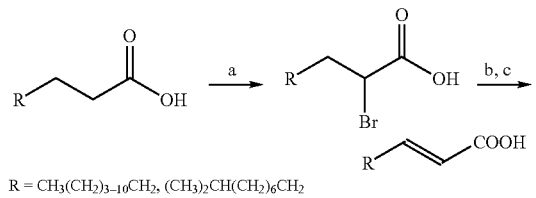

Scheme 2

In Scheme 2, (a) Br$_2$, HBr, H$_2$O, 2 h, ~55% yield; (b) KOBu$^{tert}$, tert-BuOH, 3 h; (c) 1N HCl, >90% yield.

Referring to FIG. 2, compounds 1 and 5-9 were synthesized according to Scheme 1, compounds 2 and 11-15 were synthesized according to Scheme 2, compound 3 was synthesized as previously reported[16], and the others were obtained commercially from Sigma-Aldrich, USA. All the synthetic compounds were characterized by $^1$H NMR, $^{13}$C NMR, and mass spectroscopy.

Example 2

An in vitro bioassay of the inhibitory activity of the fatty acids of FIG. 2 against *C. albicans* yeast-to-mycelium transition was carried out.

*C. albicans* strain CAI4 (ATCC MYA-684) was incubated at 28° C. for 24 h with shaking in a glucose salts (GS) medium (5 g of glucose, 0.26 g of Na$_2$HPO$_4$.12H$_2$O, 0.66 g of KH$_2$PO$_4$, 0.88 g of MgSO$_4$.7H$_2$O, 0.33 g of NH$_4$Cl, 16 μg of biotin per litre) supplemented with 0.1 mg/ml of uridine.

All the *C. albicans* cells remained, in the yeast form under these conditions. The yeast cells were washed three times with GS medium before use and then were dispersed in GS medium to give a solution with a final OD$_{600}$ of 1.0.

The test compounds set out in FIG. 2 were diluted to the indicated concentrations with GS medium and were added to 100 μl of the washed *C. albicans* culture in 96-well microtitre plates, mixed and incubated at 37° C. for 6 hours (h).

The percentages of yeast cells and germ tubes (filamentous form) were determined microscopically by counting about 300 cells from three replicates. Inhibitory activity was defined as the mole concentration that gave a minimum of 90% inhibition (IC$_{90}$) relative to control.

Compounds with useful yeast-to-mycelium inhibitory activity were compounds 1, 2, 5 to 8 and 11 to 14 as shown in FIG. 2.

Example 3

Figure 3:
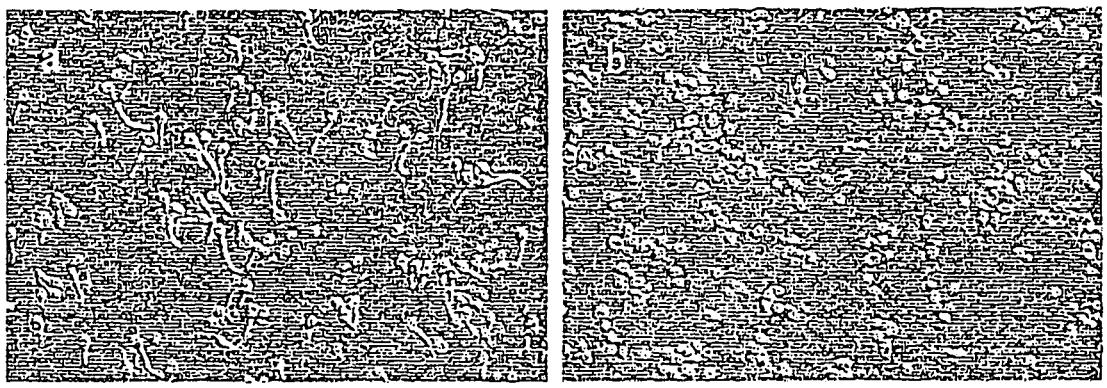
FIGS. 3a and 3b show that DSF does not affect yeast growth but inhibits the yeast-to-mycelium transition of a culture of Candida albicans (the bar indicates 30 μm).

Compound 1 was not observed to have a toxic effect on yeast cell growth even at concentrations up to 1 mM, as shown in FIG. 3*b* (the bar indicates 30 μm).

A starter culture of *C. albicans* strain CAI4 was prepared by growing the fungus at a low temperature (28° C.) in GS medium to maintain the yeast cell morphology. The culture was diluted with the same fresh medium with or without supplement of DSF and incubated at a high temperature (37° C.) which promotes yeast-to-mycelium conversion. FIG. 3a (the bar indicates 30 μm) shows that within 6 hours of incubation, the majority of C. albicans cells formed germ tubes in the absence of DSF, whereas addition of 30 μM DSF to the culture of C. albicans completely abolished yeast to-mycelium transition (FIG. 3b). No toxic effect on yeast cell growth was noticed even when DSF concentration was increased up to 1 mM. The synthetic DSF was indistinguishable with the natural DSF in inhibition of germ tube formation.

The above describes some preferred embodiments of the present invention and indicates several possible modifications but it will be appreciated by those skilled in the art that other modifications can be made without departing from the scope of the invention.

REFERENCES

1. Odds, F. C. *Candida* and *Candidosis*, 1998, Ballière Tindall, London
2. Corner, B. E., Magee, P. T. *Candida* pathogenesis: unraveling the threads of infection. *Curr. Biol* 1997, 7, R691-R694
3. Madhani, H. D., Fink, G. R. The control of filamentous differentiation and virulence in fungi. *Trends Cell Biol* 1998, 8, 348-353
4. Brown, A. J. P.; Gow, N. A. R. Regulatory networks controlling *Candida albicans* morphogenesis. *Trends Microbiol.* 1999, 7, 333-338
5. Staib, P.; Kretschmar, M.; Nichterlein, T.; Hol H.; Morschhauser, J. Differential activation of a *Candida albicans* virulence gene family during infection. *Proc. Natl Acad Sci.* U.S.A. 2000, 97, 6102-6107
6. Navarro-Garcia, F.; Sánchez, M.; Nombela, C.; Pla, J. Virulence genes in the pathogenic yeast *Candida albicans*. *FEMS Microbial. Rev.* 2001, 25, 245-268.
7. Liu H. Co-regulation of pathogenesis with dimorphism and phenotypic switching in *Candida albicans*, a commensal and a pathogen. *Int. J Med Microbiol.* 2002, 292, 299-311.
8. Mittendorf, J.; Kunisch, F.; Matzke, M.; Militzer, H.-C.; Schmidt, A.; Schonfeld, W. Novel antifungal beta-amino acids: synthesis and activity against *Candida albicans*. *Bioorg. Med. Chem. Lett.* 2003, 13, 433-436
9. McGeady, P.; Wansley, D. L.; Logan, D. A. Carvone and perillaldehyde interfere with the serum-induced formation of filamentous structures in *Candida albicans* at substantially lower concentrations than those causing significant inhibition of growth. *J. Nat. Prod* 2002, 65, 953-955
10. Oh, K.-B.; Miyazawa, H.; Naito, T.; Matsuoka, H. Purification and characterization of an autoregulatory substance capable of regulating the morphological transition in *Candida albicans*. *Proc. Natl. Acad. Sci.* U.S.A. 2001, 98, 4664-4668
11. Kim, S.; Kim, E.; Shin, D. S. Kang, H.; Oh, K.-B. Evaluation of morphogenic regulatory activity of farnesoic acid and its derivatives against *Candida albicans* dimorphism. *Bioorg. Med Chem. Lett.* 2002, 12, 895-898
12. Hornby, J. M.; Jensen, E. C.; Lisec, A. D.; Tasto, J. J.; Jahnke, B.; Shoemaker, R.; Dussault, P.; Nickerson, K. W. Quorum sensing in the dimorphic fungus *Candida albicans* is mediated by farnesol. *Appl. Environ. Microbiol.* 2001, 67, 2982-2992
13. Barber, C. E.; Tang, J. L.; Feng, J. X.; Pan, M. Q.; Wilson, T. J. G.; Slater, H.; Dow, J. M.; Williams, P.; Daniels, M. J. A novel regulatory system required for 20 pathogenicity of *Xanthomonas campestris* is mediated by a small diffusible signal molecule. *Mol Microbiol.* 1997: 24, 555-566
14. Rappe, C.; Adeström, R. Favorsky rearrangements IV. The preparation of some cis-α,β-unsaturated acids. *Acta Chem Scand.* 1965, 19, 383-389 10
15. Rappe, C. *Org. Synth.* 1973, 53, 123-127
16. Brown, B. C. D.; Hughes, R. M.; Keily, J.; Kenney, A. Diastereoselective synthesis of tetrahydrofuran-containing fragments by the permanganate oxidation of 1,5,9-trienes. *Chem. Coinmun.* 2000, 1735-1736
17. Forman, B, M.; Goode, E.; Chen, J.; Oro, A. E.; Bradley, D. J.; Perlmann, T.; Noonan, D. J.; Burka, L. T.; McMorris, T.; Lamph, W. W.; Evans, R. W.; Weinberger, C. Identification of a nuclear receptor that is activated by farnesol metabolites. *Cell* 1995, 81, 687-693
18. Weinberger, C. A model for farnesoid feedback control in the mevalonate pathway. *Trends Endocrinol. Metab.* 1996, 7, 1-6
19. Chiang, J. Y. L. Bile acid regulation of gene expression: roles of nuclear hormone receptors. *Endocrine reviews* 2002, 23, 443-463

What we claim is:
1. Cis or trans 11-methyl-2-dodecenoic acid.
2. A pharmaceutical composition comprising cis or trans 11-methyl-2-dodecenoic acid and a pharmaceutically acceptable carrier.

* * * * *